United States Patent [19]

Thompson

[11] 4,350,155
[45] Sep. 21, 1982

[54] BODY IMPLANTABLE MEDICAL INFUSION SYSTEM

[75] Inventor: Howard J. Thompson, New Richmond, Wis.

[73] Assignee: Medtronic, Inc., Minneapolis, Minn.

[21] Appl. No.: 136,811

[22] Filed: Apr. 2, 1980

[51] Int. Cl.³ .................... A61M 31/00; F16K 13/04; F16K 17/36
[52] U.S. Cl. .................. 128/213 R; 128/214 E; 128/214 F; 128/260; 137/73
[58] Field of Search ............. 128/213 R, 214 F, 260, 128/214 E, DIG. 12; 137/76, 75, 72, 73, 460

[56] References Cited

U.S. PATENT DOCUMENTS

| | | | |
|---|---|---|---|
| 3,275,012 | 9/1966 | Howard et al. | 137/76 |
| 3,690,336 | 9/1972 | Drum | 137/75 |
| 3,837,339 | 9/1974 | Aisenberg et al. | 128/213 |
| 3,951,147 | 4/1976 | Tucker et al. | 128/214 F |
| 4,077,405 | 3/1978 | Haerten et al. | 128/213 |
| 4,128,105 | 12/1978 | Follett | 137/73 |
| 4,221,219 | 9/1980 | Tucker | 128/260 |
| 4,239,040 | 12/1980 | Hosoya et al. | 128/260 |

FOREIGN PATENT DOCUMENTS 484768 10/1976 U.S.S.R. ................. 137/76

Primary Examiner—Robert Peshock
Assistant Examiner—Michael J. Foycik, Jr.
Attorney, Agent, or Firm—Schroeder, Siegfried, Vidas, Steffey & Arrett

[57] ABSTRACT

A body implantable medical infusion system including an infusate reservoir, a system for regulating infusate discharge and a catheter for delivery of discharged infusate to the desired infusion site. An unregulated infusate discharge is prevented, in a preferred embodiment, by a normally open valve positioned intermediate the pump and the catheter, the valve closing in response to the sensing of unregulated infusate. A sensor, to which the valve responds, may be positioned at the output of the pump or at any other location within the system to sense infusate leakage. The valve may be additionally closed in response to an externally generated signal.

9 Claims, 3 Drawing Figures

BODY IMPLANTABLE MEDICAL INFUSION SYSTEM

BACKGROUND OF PRIOR ART

Body implantable medical infusion systems are known to the prior art. Typically, such systems include an infusate reservoir and a system for providing a regulated discharge of infusate, the discharge being delivered to a desired infusion site via a catheter.

One prior art example of a body implantable medical infusion system is disclosed in U.S. Pat. No. 3,951,147 issued Apr. 20, 1976, to Tucker et al for IMPLANTABLE INFUSATE PUMP which is hereby incorporated herein by reference. The Tucker pump is a mechanical device and includes a pressurized reservoir, the pressure on the reservoir forcing infusate through the outlet catheter to the infusion site. Various infusate flow controllers are disclosed in the Tucker patent which operate on the flow path of the infusate to regulate the amount of discharge. In addition, Tucker discloses the use of a shut-off valve which can be manipulated by means of external force or energy to cut off the infusate flow.

BRIEF SUMMARY OF THE INVENTION

The present invention provides, within a body implantable medical infusion system, apparatus for preventing an unregulated infusate discharge. The system includes an infusate reservoir, means for regulating infusate discharge and a catheter for delivering the discharged infusate to a desired infusion site. In a preferred embodiment, a normally open valve is controlled to close in response to the sensing of infusate leakage. A sensor may be positioned adjacent the outlet of the infusate discharge regulating means or, alternatively, at any other possible leakage location. The valve may also be closed via an externally generated signal.

Specifically, the valve may be formed of a valving member normally spring biased to a closed position but restrained in an open position via a wire of bismuth or other low melting point material. The biasing may be effected by a coil spring in compression and surrounding the restraining wire such that a current passed through the spring will result in a heating of the spring and a melting of the restraining wire to release the valve to assume the closed position. The restraining wire may, itself, be a part of the electrical circuit to further facilitate its melting. Current control through the spring and restraining wire may be maintained by a normally open switch, the switch closing on the occurrence of a predetermined event. The event may be either the detection of an externally generated signal, as when a malfunction is suspected, or on the detection of infusate leakage by any appropriate sensor. The valve is positioned to block a flow of infusate to the output catheter and, in a preferred embodiment, is positioned between the apparatus which regulates infusate flow and the catheter.

DETAILED DESCRIPTION OF THE INVENTION

Figure 1:
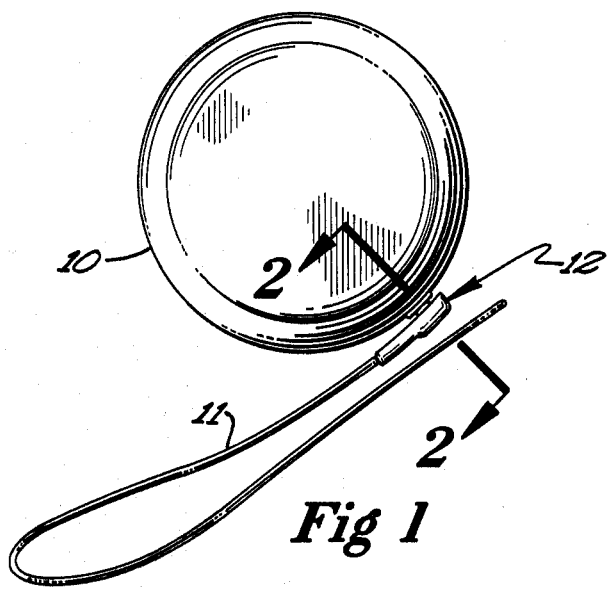
FIG. 1 illustrates a body implantable medical infusion of a type to which the present invention is directed.

FIG. 1 illustrates a body implantable medical infusion system including a housing 10 and catheter 11, the catheter 11 being connected to the housing 10 via a coupling device or connector assembly 12. The housing 10 houses an infusate reservoir and a system for regulating the infusate discharge from the housing 10 to the catheter 11, the catheter 11 delivering discharged infusate to the desired infusion site, in known manner. The system for regulating infusate discharge may be an active element such as a roller pump or, alternatively, may be a device that operates on the basis of flow restriction as in the incorporated Tucker patent. In any event, the amount of infusate to be delivered is regulated with the regulated amount being delivered via the catheter 11.

In the event that infusate manages to bypass the regulating system, as by the rupture of an internal tubing, for example, the amount of infusate discharged to the catheter may exceed the desired amount. Indeed, the amount of discharged infusate may exceed that which is medically safe. In either event, the present invention provides a system for preventing an unregulated infusate discharge to the catheter 11.

Figure 2:
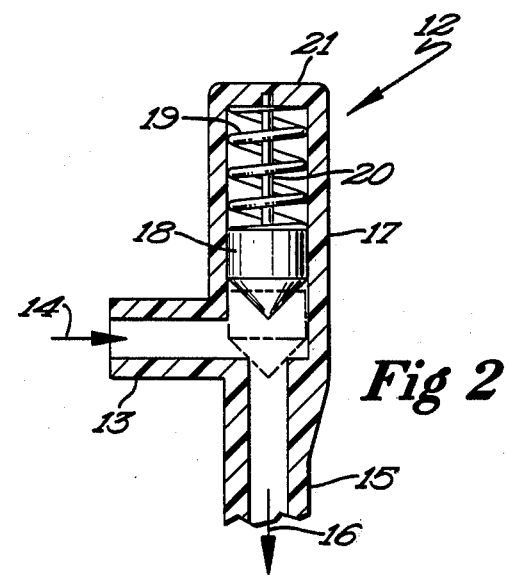
FIG. 2 illustrates a cross-section taken along the line 2—2 in FIG. 1.

With reference to FIG. 2, there is illustrated a cross-section taken along the line 2—2 in FIG. 1 and, specifically, a cross-section of the connector assembly 12. The connector assembly 12 includes one leg 13 adapted for connection to the housing 10 to receive a regulated flow of infusate in the direction of the arrow 14. A second leg 15 is adapted for connection to the catheter 11 for delivery of a regulated infusate discharge to the catheter 11 in the direction of the arrow 16. A third leg 17 contains an internal chamber which houses a valving member 18, compression spring 19 and restraining member 20. The compression spring 19 is compressed between the valving member 18 and end wall 21 of the chamber of leg 17 so as to move an unrestrained valving member 18 to the position illustrated in phantom in FIG. 2, valving member 18 totally blocking flow into the leg 15 in the position illustrated in phantom. However, the restraining member 20 engages both the end wall 21 and the valving member 18 to maintain the valving member 18 within the leg 17 in a normally open position. As will be described more fully below, a malfunction within the housing 10 will result in a severing of the restraining member 20, either manually or automatically, to allow the valving member 18 to be moved under the influence of the spring 19 into the blocking relationship illustrated in phantom in FIG. 2.

Figure 3:
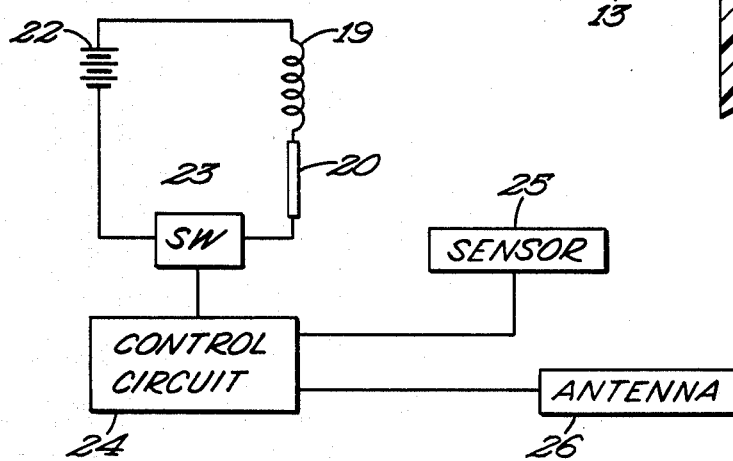
FIG. 3 diagramatically illustrates the electrical interconnection of those components forming a portion of the embodiment of FIG. 2.

FIG. 3 illustrates the electrical interconnection between the spring 19 and restraining member 20, those elements being serially connected with a power supply 22 and a switch 23. The compression spring 19 is formed of a thermal wire which heats when it is conducting current. The restraining member 20 is formed as a wire of a low melting point material such as bismuth. As illustrated in FIG. 2, the spring 19 surrounds the restraining wire 20 and generates sufficient heat to melt the restraining wire 20 when the switch 23 is closed. The restraining wire 20 is serially connected with the spring 19, power supply 22 and switch 23 to further contribute to the heating of the restraining wire 20. Switch 23 is normally open, to be closed on the occurrence of a predetermined event.

The switch 23 is operated under the control of a control circuit 24, the control circuit having as inputs a sensor 25 and an antenna 26. Sensor 25 may be one or more devices capable of sensing the presence of liquid or an increase in humidity and are positioned so as to detect infusate leakage within the housing 10 (See FIG. 1). For example, if infusate discharge is regulated by a pump, such as a roller pump housed within the housing 10, a desirable sensor location would be at the pump output. Alternatively, a sensor 25 may be positioned at other likely infusate leakage sites. On detection of infusate leakage, by sensor 25, switch 23 is closed under the control of control circuit 24, in known manner. The closing of switch 23 results in a heating of the material forming the compression spring 19, as well as the restraining wire 20, causing the restraining wire 20 to melt and release the valving member 18 to close the infusate flow path within the leg 15 of the connector assembly 12. This also opens the connection between the serially connected elements. Also, in the event that an infusion system malfunction is suspected, an externally generated signal, such as an RF signal, may be transmitted to the implanted device to be detected by antenna 26, the signal detected by antenna 26 resulting in a closing of switch 23 by control circuit 24, also in known manner. Thus, a medical infusion system in accordance with the present invention prevents an unregulated infusate discharge through the use of the normally open valve which is closed on the detection or suspicion of infusate leakage. As illustrated, the valve is connected intermediate the infusate flow regulator and the output catheter to block the flow of infusate to the catheter, when necessary. The system may respond automatically or be responsive to an externally generated signal.

Obviously, many modifications and variations of the present invention are possible in light of the above teachings. For example, it may be necessary to provide a seal between the valving member 18 and the internal chamber of leg 17 to prevent a flow of infusate behind the valving member 18. In addition, the valve may be positioned elsewhere than within the connector assembly 12. For example, the valve may be positioned within the housing 10 in close proximity to the connection for the connector assembly 12 to block the flow of infusate to the catheter 11. Additionally, other types of valves and valve actuating mechanisms may be employed without departing from the scope of the present invention. It is therefore to be understood that, within the scope of the appended claims, the invention may be practiced otherwise than as specifically described.

I claim:

1. In a body implantable medical infusion system of the type having an infusate reservoir, means for regulating infusate discharge and catheter means for delivering discharged infusate to a desired infusion site, the improvement which comprises further means for preventing an unregulated infusate discharge including normally open valve means, means for sensing the presence of unregulated infusate and means responsive to said sensing means for closing said valve means.

2. The body implantable medical infusion system of claim 1 further comprising means for closing said valve means via an externally generated signal.

3. The body implantable medical infusion system of claim 2 further comprising means for sensing the presence of unregulated infusate and means responsive to said sensing means for closing said valve means.

4. The body implantable medical infusion system of claim 1 wherein said infusate discharge regulating means comprises pump means having an infusate input and output, said sensing means sensing the presence of infusate adjacent the pump means output.

5. The body implantable medical infusion system of claim 4 wherein said valve means is connected intermediate said pump means and said catheter means.

6. The body implantable medical infusion system of claim 5 further comprising means for closing said valve means via an externally generated signal.

7. In a body implantable medical infusion system of the type having an infusate reservoir, means for regulating infusate discharge and catheter means for delivering discharged infusate to a desired infusion site, the improvement which comprises further means for preventing an unregulated infusate discharge including means for blocking the flow of infusate to said catheter means on the occurrence of a predetermined event, and further comprising means for sensing infusate leakage within said system, said predetermined event comprising sensed infusate leakage.

8. The body implantable medical infusion system of claim 7 wherein said infusate flow blocking means comprises normally open valve means.

9. The body implantable medical infusion system of claim 7 wherein said predetermined event further comprises the external generation of a preselected signal.

* * * * *